United States Patent [19]
Maetzel et al.

[11] Patent Number: 4,965,369
[45] Date of Patent: Oct. 23, 1990

[54] METHOD FOR PREPARING INDOLE CARBOXYLIC ACID DERIVATIVES

[75] Inventors: Uwe Maetzel, Burgdorf; Walter Heitmann, Burgwedel, both of Fed. Rep. of Germany

[73] Assignee: Kali-Chemie Pharma GmbH, Hanover, Fed. Rep. of Germany

[21] Appl. No.: 489,895

[22] Filed: Mar. 7, 1990

[30] Foreign Application Priority Data

Mar. 8, 1989 [DE] Fed. Rep. of Germany ....... 3907388

[51] Int. Cl.$^5$ ................... C07D 209/18; C07D 471/06
[52] U.S. Cl. ..................... 548/492; 548/430; 548/508; 546/94; 544/35; 544/101
[58] Field of Search ............. 548/430, 492, 508; 544/35, 101; 546/94

[56] References Cited

U.S. PATENT DOCUMENTS 4,736,043  4/1988  Michel et al. .................. 548/92

FOREIGN PATENT DOCUMENTS 189002   7/1986  European Pat. Off. .
0322016  6/1989  European Pat. Off. ............. 546/94
0008654  8/1989  PCT Int'l Appl. .................. 546/94
463667   3/1975  U.S.S.R. .............................. 548/492

Primary Examiner—David B. Springer
Attorney, Agent, or Firm—Foley & Lardner, Schwartz, Jeffery, Schwaab, Mack, Blumenthal & Evans

[57] ABSTRACT

A method of preparing indole carboxylic acid derivatives from aniline derivatives is described which can be carried out in a single reaction vessel without any isolation of intermediate products. The method involes reacting an aniline derivative with a soluble nitrite in an acid medium, reducing the resulting nitrosamine by treating the acidic nitrosamine containing reaction solution with zinc in the presence of sufficient acid, optionally with addition of additional acid and/or a solvent such as a lower alcohol, reacting the resulting hydrazine derivative containing solution with a lower alkyl ester of pyruvic acid to obtain a corresponding hydrazone which cyclizes to yield an indole carboxylic acid ester, and if desired, hydrolyzing the ester to obtain the corresponding carboxylic acid.

17 Claims, No Drawings

METHOD FOR PREPARING INDOLE CARBOXYLIC ACID DERIVATIVES

BACKGROUND OF THE INVENTION

The present invention relates to the preparation, from aniline derivatives, of indole carboxylic acid derivatives which are useful as intermediate products in the pharmaceutical industry.

Indole carboxylic acid derivatives may be used as intermediate products in preparing pharmaceutically usable active substances. For instance, indole carboxylic acid derivatives can be reacted with bicyclic alkaloid radicals having an 8-azabicyclo-[3,2,1]-octane type of structure, for example with tropine or with 3-amino-8-methyl-8-azabicyclo-[3,2,1]octane, to yield pharmacologically active substances having 5-HT$_3$-antagonistic properties, which are suitable for the treatment of serotonin-induced gastrointestinal complaints (see European Patent No. 0 189 002 A2). In particular, pharmacologically active substances which can be obtained from 1,7-fused indole carboxylic acid derivatives and the aforementioned bicyclic alkaloid radicals are strong and selective antagonists of neuronal 5 HT receptors, which are useful in treating complaints induced by overstimulation of these receptors (see European Patent No. 0 322 016 A1). Pharmacologically active substances with CCK-antagonistic properties can be obtained by reacting 1,7-fused 1H-indole-2-carboxylic acid derivatives with 3-amino-1,4-benzodiazepine derivatives.

Indole carboxylic acid derivatives may, inter alia. be prepared by reacting phenylhydrazine derivatives with pyruvic acid derivatives. The phenylhydrazine derivatives required for this purpose must themselves be obtained from corresponding phenylnitrosamine derivatives. The latter are produced by nitration of aniline derivatives.

SUMMARY OF THE INVENTION

In is the object of the present invention to develop a new method of preparing indole carboxylic acid derivatives from aniline derivatives.

Another object of the present invention is to provide an improved method of preparing indole carboxylic acid derivatives which avoids the drawbacks of prior production methods.

It is also an object of the present invention to provide a method of preparing indole carboxylic acid derivatives which avoids any need for isolation of intermediate products and does not require handling of nitrosamine and phenylhydrazine derivatives.

A further object of the present invention is to provide a method of preparing indole carboxylic acid derivatives which can be carried out in a single reaction vessel.

These and other objects of the invention have been achieved by providing a method of preparing an indole carboxylic acid compound corresponding to the Formula I,

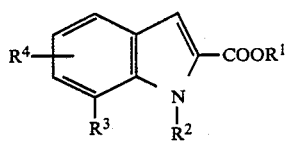

wherein
R$^1$ represents hydrogen or lower alkyl,
R$^2$ represents lower alkyl or a carbocyclic aryl group or carbocyclic aryl lower alkyl group which groups may optionally be substituted by lower alkyl, halogen or lower alkoxy, and
R$^3$ represents hydrogen, lower alkyl, lower alkoxy or a carbocyclic aryl group or carbocyclic aryl lower alkyl group which groups may optionally be substituted by lower alkyl, halogen or lower alkoxy, or
R$^2$ and R$^3$ together form an alkylene chain with 2 to 4 carbon atoms which may optionally be substituted by lower alkyl, and to which a 5-6-member carbocyclic ring may optionally be fused, or R$^2$ and R$^3$ together form an —X—CH$_2$—CH$_2$— chain, wherein X is bonded to the phenyl ring of the indole structure and is oxygen or sulfur, and
R$^4$ represents hydrogen, lower alkyl, lower alkoxy, halogen or trifluoromethyl,
comprising the steps of:
(a) reacting an aniline compound corresponding to the Formula II,

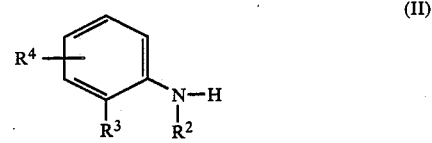

wherein R$^2$, R$^3$ and R$^4$ have the above meanings, with an alkali metal nitrite at temperatures in the range from about 0° to about 30° C. in an acidic medium containing an amount of acid at least equivalent to the compound of Formula II, to produce a corresponding nitrosamine derivative;
(b) while cooling to maintain the temperature in the range from about 0° to about 30° C., adding to the nitrosamine derivative-containing, acidic reaction medium from step (a), a quantity of metallic zinc which is at least twice molar relative to the compound of Formula II, and if needed to assure the presence of a sufficient quantity of acid adding additional acid, wherein the adding of at least one reactant selected from the group consisting of zinc and additional acid is carried out sufficiently slowly to prevent the temperature of the resulting reaction mixture from exceeding about 30° C., and allowing the resulting reaction mixture to react in the presence of a sufficient amount of acid and for a time sufficient to reduce the nitrosamine derivative to the corresponding hydrazine derivative, and
(c) reacting a hydrazine derivative containing reaction mixture obtained from step b) with a pyruvic acid lower alkyl ester at temperatures in the range from about room temperature to about 120° C. to obtain an indole carboxylic acid ester derivative corresponding to Formula Ia,

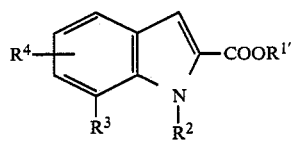

wherein R$^2$ and R$^3$ have the above meanings and R$^{1\prime}$ is lower alkyl, and, if desired, subsequently hydrolyzing the indole carboxylic acid ester derivative to obtain the corresponding free acid.

DETAILED DESCRIPTION OF THE PREFERRED EMBODIMENTS

A method has now been devised by which aniline derivatives can be reacted directly to indole carboxylic acid derivatives in a single-reaction vessel process without isolation of the resulting intermediate products.

The invention thus relates to a method for the preparation of indole carboxylic acid derivatives of the general Formula I,

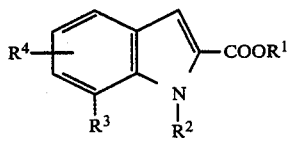

wherein
$R^1$ is hydrogen or lower alkyl,
$R^2$ is lower alkyl or a carbocyclic aryl group or carbocyclic aryl lower alkyl group which groups may optionally be substituted by lower alkyl, halogen or lower alkoxy, and
$R^3$ is hydrogen, lower alkyl, lower alkoxy or a carbocyclic aryl group or carbocyclic aryl lower alkyl group which groups may optionally be substituted by lower alkyl, halogen or lower alkoxy, or
$R^2$ and $R^3$ together form an alkylene chain with 2 to 4 carbon atoms which may optionally be substituted by lower alkyl, and to which a 5-6-member carbocyclic ring may optionally be fused, or $R^2$ and $R^3$ together form an $-X-CH_2-CH_2-$ chain, wherein X is bonded to the phenyl ring of the indole structure and is oxygen or sulfur, and
$R^4$ is hydrogen, lower alkyl, lower alkoxy, halogen or trifluoromethyl,
wherein
(a) aniline derivatives of the general Formula II,

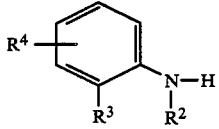

wherein $R^2$, $R^3$ and $R^4$ have the above meanings, are reacted with an alkali metal nitrite at temperatures of between 0° and 30° C. in a liquid organic acid or in an aqueous medium containing a quantity of an acid at least equivalent to the compound of Formula II and optionally a water-miscible organic solvent, to produce the corresponding nitrosamine,
(b) optionally additional acid is added to the nitrosamine-containing reaction solution obtained under a) until a quantity of acid of at least 5 equivalents acid relative to the compound of Formula II is present, and optionally with the addition of a water-miscible organic solvent a quantity of metallic zinc which is at least twice molar relative to the compound of Formula II is added, the zinc being added in portions into the solution already containing the entire quantity of acid or after the addition of the zinc the acid being added in portions, the adding being done with cooling and so slowly that a temperature of between 0° and 30° C. is maintained in the reaction solution, and the reaction mixture is allowed to react at this temperature for a time sufficient for the reduction of the nitrosamine to the corresponding hydrazine, and optionally additional acid is added in order to complete the reaction of an excess of metallic zinc which is present in the reaction mixture,
(c) the hydrazine-containing reaction solution obtained under b) is reacted with a pyruvic acid lower alkyl ester at temperatures of between room temperature and 120° C. and if desired subsequently the resulting indole carboxylic acid ester derivatives of Formula Ia,

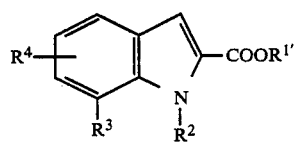

wherein $R^2$ and $R^3$ have the above meanings and $R^{1'}$ is lower alkyl, are hydrolyzed to produce the free acid.

The method according to the invention is particularly suitable for the preparation of indole-2-carboxylic acid derivatives and 4H-pyrrolo[3,2,1-ij]-5,6-dihydroquinolin-2-carboxylic acid derivatives.

According to the method of the invention, the starting aniline derivative of Formula II is first reacted in acidic medium with an alkali metal nitrite such as sodium nitrite. In the process, a nitrosamine of Formula III,

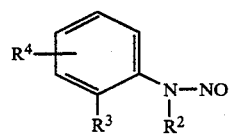

wherein $R^2$, $R^3$ and $R^4$ have the above meanings, and which corresponds to the compound of Formula II, forms in the reaction solution. The reaction takes place in an acidic medium, that is to say, the pH value of the medium should be less than pH=4. The aniline derivative of Formula II may for instance be dissolved in an organic acid or dissolved partially or completely in an acid/water mixture, to which may optionally be added another organic solvent which is water-miscible, and an aqueous alkali metal nitrite solution can then be added to this reaction solution with cooling. Advantageously, a quantity which is equimolar relative to the compound of Formula II or an only slight excess (up to 5%) of sodium nitrite is used.

Suitable acids are those organic and inorganic acids which can be mixed with water and which are strong enough to react with metallic zinc to form nascent hydrogen. The acid strength may vary depending on the nature and stability of the starting anilines and of the phenylhydrazine derivatives which are to be formed intermediately therefrom. Suitable organic acids include lower aliphatic carboxylic acids optionally substituted by halogen or trifluoromethyl, for instance acetic acid or haloacetic acids. Examples of suitable inorganic acids include hydrogen halide acids or sulfuric acid. Preferably, acetic acid, aqueous hydrochloric acid or mixtures thereof are used.

In order to improve solubility, another organic solvent which is inert under the reaction conditions and which is water-miscible may be added to the reaction mixture if desired during the reaction with the nitrite, or alternatively only later during the reduction with metallic zinc. Lower alkyl alcohols are particularly suitable for this purpose. Liquid organic acids may themselves also serve as solvents. Addition of alcohol may be advantageous, particularly if the acid content of the reaction mixture is largely formed of aqueous inorganic acids.

The reaction with the alkali metal nitrite takes place at temperatures of between about 0° and about 30° C., preferably between about 5° and about 20° C. The reaction time may be between about 30 minutes and two hours.

The concentration of the starting aniline derivative in the reaction solution is not critical for the process to operate and may be varied depending on the solubility of the compounds. The aniline derivative may be completely dissolved in the reaction solution or alternatively may be only partially dissolved and partially suspended. 0.5 to 2-molar, in particular about 1 to 1.5-molar, solutions of the starting substance have proved advantageous.

For the reduction of the nitrosamine, metallic zinc, preferably metallic zinc powder, is added to the reaction mixture. A molar amount of metallic zinc is used which is at least twice the molar amount of the starting compound of Formula II. Preferably an excess, for instance a 2 to 5-fold molar amount, particularly a 2.5 to 4-fold molar amount, is used.

Furthermore, if after the nitrosamination has ended the reaction mixture does not contain a sufficient amount of acid for the subsequent reduction of the nitrosamine to the corresponding hydrazine, normally at least 4, and preferably at least 5, equivalents of acid, relative to the starting compound, at least so much additional acid should be added to the reaction mixture that a quantity of acid of at least 4, and preferably 5, equivalents of acid relative to the starting compound is achieved. When using predominantly inorganic acids, quantities of acid of, for instance, 5 to 9 equivalents relative to the starting compounds of Formula II are suitable. If organic acids are used also as solvents, of course even far larger quantities thereof may be present in the reaction mixture.

In this reaction step, it is possible to proceed so that initially the entire quantity of acid is added to the reaction mixture and then the zinc is added in portions with cooling, preferably ice cooling, so slowly that a temperature of between about 0° and about 30° C., preferably between about 5° and about 25° C., is maintained in the reaction mixture. However, the zinc may also be added first and then the remaining acid may be added so slowly, with cooling, that the temperature does not exceed about 30° C. The addition of zinc and acid to the reaction mixture may for instance take place distributed over a period of 1 to 3 hours. After the addition has ended, the reaction mixture is advantageously stirred for an additional time, preferably at room temperature, in order to achieve a complete conversion of the nitrosamine into the corresponding phenylhydrazine of Formula IV,

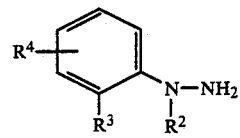

wherein $R^2$, $R^3$ and $R^4$ have the above meanings.

In order to ensure complete reaction of an excess of metallic zinc present in the reaction mixture and if desired to dissolve the resulting zinc salts completely, it may be advantageous to add more acid, for instance aqueous hydrochloric acid, to the reaction mixture.

Then the reaction mixture is reacted with a pyruvic acid lower alkyl ester of Formula V,

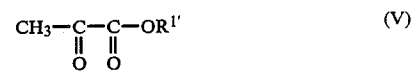

wherein $R^{1'}$ has the above meaning. A quantity which is equimolar relative to the compound of Formula II or alternatively up to 3 times excess of pyruvic acid lower alkyl ester, in particular pyruvic acid ethyl ester, may be used. The reaction may be carried out at temperatures between room temperature and 120° C., preferably at the boiling temperature of the reaction mixture. The reaction time may for instance be between 0.5 and 2 hours. Upon the addition of the pyruvic acid ester to the reaction mixture containing the phenylhydrazine compound of Formula IV, the hydrazone compound of Formula VI,

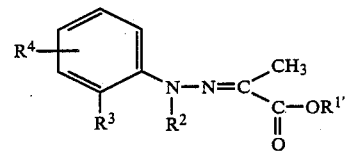

wherein $R^{1'}$, $R^2$, $R^3$ and $R^4$ have the above meanings, is produced intermediately, and further condenses to the ester of Formula Ia under the reaction conditions.

The compounds of Formula Ia may be isolated from the reaction mixture by known techniques and purified in known manner. For instance, the compounds may be extracted from the reaction mixture with a halogenated hydrocarbon, preferably dichloromethane. If desired, the crude product obtained after removing the solvent may be purified in known manner using chromatography.

The esters of Formula Ia may be hydrolyzed in known manner to the corresponding acids.

Compared with hitherto commonly used methods for the preparation of indole carboxylic acid derivatives from corresponding aniline derivatives, the method according to the invention has the advantage that the reaction, which passes through a plurality of intermediate products, is a so-called "one-pot process," which is carried out in a single reaction vessel in such a way that no isolation of intermediate products is necessary. Thus, handling of the nitrosamine and phenylhydrazine derivative intermediates can be avoided.

Compounds of Formula II are known or can be prepared according to known methods.

The following examples are intended to illustrate the invention in further detail, without limiting its scope.

EXAMPLE 1:

4H-Pyrrolo[3,2,1-ij]-5,6-dihydroquinolin-2-carboxylic acid ethyl ester.

150 g 1,2,3,4-tetrahydroquinoline were dissolved in 1.25 glacial acetic acid. To the solution was added a solution of 80 g sodium nitrite in 300 ml water with cooling in an ice bath to approximately 15° C. internal temperature, and the reaction mixture was stirred further for 45 minutes. To the reaction solution containing the resulting N-nitroso-1,2,3,4-tetrahydroquinoline were added 300 g zinc dust in portions over 1.5 hours, the reaction mixture being maintained at an internal temperature of 15°≈30° C. by cooling in an ice bath. Then 1.75 l water and 1.25 l 32% aqueous hydrochloric acid were added to the mixture, and it was stirred for another 1.5 hours. To the acid reaction mixture containing the resulting N-amino-1,2,3,4-tetrahydroquinoline and the zinc salt were added 130 g pyruvic acid ethyl ester, and the mixture was heated under reflux for 1.5 hours, and then allowed to stand for another 16 hours. In so doing the intermediately formed hydrazone was immediately condensed in situ to 4H-pyrrolo[3,2,1-ij]-5,6-dihydroquinolin-2-carboxylic acid ethyl ester. The reaction mixture was worked up by extracting twice with a total of 5 l dichloromethane, the dichloromethane extracts were combined, washed twice with a total of 1 l water, dried over sodium sulfate and reduced in volume. 280 g of crude 4H-pyrrolo[3,2,1-ij]-5,6-dihydroquinolin-2-carboxylic acid ethyl ester were obtained, which were purified by chromatography on silica gel using dichloromethane as an eluent. 151.8 g of the purified title compound with a melting point of 70°-72° C. were obtained.

EXAMPLE 2:

4H-Pyrrolo[3,2,1-ij]-5,6-dihydroquinolin-2-carboxylic acid.

39 g 4H-Pyrrolo[3,2,1-ij]-5,6-dihydroquinolin-2-carboxylic acid ethyl ester were dissolved in 40 ml ethanol, and this solution was added at room temperature to a solution of 11.3 g potassium hydroxide in a mixture of 20 ml water and 145 ml ethanol. The reaction mixture was stirred for 90 minutes at room temperature, and then cooled to 10° C. The resulting solids were suction filtered and washed three times with 30 ml ethanol in each case. The mother liquor was reduced to half volume, and the solids produced thereby were likewise separated off and washed with ethanol.

All the solids were then dissolved in 150 ml water, and the title compound was precipitated therefrom by acidifying the solution with concentrated hydrochloric acid to pH 1 to 2. The resulting acid was separated off, washed three times with 40 ml water in each case and dried at 60° C. 32.4 g of the title compound with a melting point of 212°-213° C. (decomp.) were obtained.

EXAMPLE 3:

4H-Pyrrolo[3,2,1-ij]-5,6-dihydroquinolin-2-carboxylic acid ethyl ester.

40 g tetrahydroquinoline were dissolved in a mixture of 29.5 ml concentrated hydrochloric acid (32%) and 140 ml water at room temperature. A solution of 21.3 g sodium nitrite in 60 ml water was added to this solution in drops, during cooling in an ice bath, in such a manner that the temperature was maintained between 10° and 20° C. Then the reaction mixture was stirred for another 40 minutes without cooling. Then 49 g zinc powder were added. The reaction mixture was cooled to 15° C. 177 ml of concentrated hydrochloric acid were added slowly in drops, with the temperature of the reaction mixture being maintained within the range of 15°-30° C.

After the zinc had reacted completely, 0.4 l ethanol were added, and the reaction mixture was heated to the boiling point. Then 35.9 g pyruvic acid ethyl ester were added in drops within 30 minutes. After the addition had ended, the reaction mixture was stirred for another 60 minutes at boiling temperature and then allowed to stand for 12 hours at room temperature. Then the alcohol was distilled off under reduced pressure, and the remaining aqueous reaction mixture was extracted with toluene. The toluene extract was washed with water, dried over sodium sulfate and reduced in volume. The residue containing the crude title compound was purified by chromatography on silica gel. 28.7 g of the purified title compound with a melting point of 70°-72° C. were obtained.

EXAMPLE 4:

1-Methylindol-2-carboxylic acid ethyl ester.

30 g N-methylaniline were dissolved in 300 ml glacial acetic acid, and a solution of 19.9 g sodium nitrite in 75 ml water was added in drops to the solution at a temperature of 10°-20° C. with ice cooling. Then stirring was continued for 20 minutes at 10°-20° C. Then, for approximately 40 minutes, 75 g zinc dust were added in portions to the reaction solution containing the resulting N-nitroso-N-methylaniline during further cooling, with the reaction temperature being maintained below 25° C. Then 720 g N-hydrochloric acid were added to the mixture, and stirring was continued for one hour. The acidic reaction mixture containing the resulting N-amino-N-methylaniline and the zinc salt was heated to 70° C. 34 g pyruvic acid ethyl ester were added in drops, and the mixture was stirred further for another 50 minutes at 70° C. and then allowed to stand for 16 hours at room temperature. In the process, the intermediately formed hydrazone was immediately condensed in situ to 1-methylindol-2-carboxylic acid ethyl ester. The reaction mixture was worked up by extracting three times with a total of 1.5 l toluene. The combined toluene extracts were washed twice with a total of 500 ml water, dried over sodium sulfate and reduced in volume. 360 g of crude 1-methylindol-2-carboxylic acid ethyl ester were obtained, which were purified by chromatography on silica gel using dichloromethane as an eluent. The purified product was crystallized from ethanol/petroleum ether. 27.2 g 1-methylindol-2-carboxylic acid ethyl ester with a melting point of 62°-64° C. were obtained.

The foregoing description and examples have been set forth merely to illustrate the invention and are not intended to be limiting. Since modifications of the described embodiments incorporating the spirit and substance of the invention may occur to persons skilled in the art, the scope of the invention should be construed to include all modifications falling within the ambit of the appended claims and equivalents thereof.

What is claimed is:

1. A method of preparing an indole carboxylic acid compound corresponding to the Formula I,

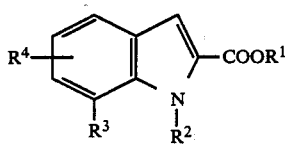 (I)

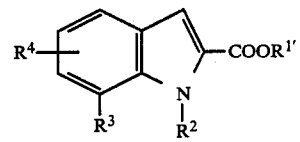 (Ia)

wherein
R[1] represents hydrogen or lower alkyl,
R[2] represents lower alkyl or a carbocyclic aryl group or carbocyclic aryl lower alkyl group which groups may optionally be substituted by lower alkyl, halogen or lower alkoxy, and
R[3] represents hydrogen, lower alkyl, lower alkoxy or a carbocyclic aryl group or carbocyclic aryl lower alkyl group which groups may optionally be substituted by lower alkyl, halogen or lower alkoxy, or
R[2] and R[3] together form an alkylene chain with 2 to 4 carbon atoms which may optionally be substituted by lower alkyl, and to which a 5-6-member carbocyclic ring may optionally be fused, or R[2] and R[3] together form an —X—CH$_2$—CH$_2$— chain, wherein X is bonded to the phenyl ring of the indole structure and is oxygen or sulfur, and
R[4] represents hydrogen, lower alkyl, lower alkoxy, halogen or trifluoromethyl,
comprising the steps of:
(a) reacting an aniline compound corresponding to the Formula II,

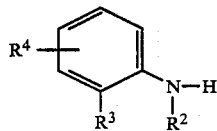 (II)

wherein R[2], R[3] and R[4] have the above meanings, with an alkali metal nitrite at temperatures in the range from about 0° to about 30° C. in an acidic medium containing an amount of acid at least equivalent to the compound of Formula II, to produce a corresponding nitrosamine derivative;
(b) while cooling to maintain the temperature in the range from about 0° to about 30° C., adding to the nitrosamine derivative-containing, acidic reaction medium from step (a), a quantity of metallic zinc which is at least twice molar relative to the compound of Formula II, and if needed to assure the presence of a sufficient quantity of acid adding additional acid, wherein the adding of at least one reactant selected from the group consisting of zinc and additional acid is carried out sufficiently slowly to prevent the temperature of the resulting reaction mixture from exceeding about 30° C., and allowing the resulting reaction mixture to react in the presence of a sufficient amount of acid and for a time sufficient to reduce the nitrosamine derivative to the corresponding hydrazine derivative, and
(c) reacting a hydrazine derivative containing reaction mixture obtained from step (b) with a pyruvic acid lower alkyl ester at temperatures in the range from about room temperature to about 120° C. to obtain an indole carboxylic acid ester derivative corresponding to Formula Ia, wherein R[2] and R[3] have the above meanings and R[1]' is lower alkyl, and, if desired, subsequently hydrolyzing the indole carboxylic acid ester derivative to obtain the corresponding free acid.

2. A method according to claim 1, wherein the alkali metal nitrite is used in an equimolar amount relative to the amount of compound of Formula II.

3. A method according to claim 1, wherein said alkali metal nitrite is sodium nitrite.

4. A method according to claim 1, wherein said acidic medium in step (a) comprises a liquid organic acid or an aqueous solution of a strong, inorganic acid.

5. A method according to claim 1, wherein said acidic medium in step (a) further comprises a water miscible organic solvent.

6. A method according to claim 5, wherein said water-miscible organic solvent is a lower alcohol.

7. A method according to claim 1, wherein the reaction mixture of step (b) comprises at least 5 equivalents of acid for each equivalent of the compound of Formula II used in step (a).

8. A method according to claim 1, further comprising prior to step (b) adding additional acid to the nitrosamine-containing reaction solution obtained in step a) until the reaction solution comprises at least 5 equivalents of acid for each equivalent of the compound of Formula II used in step (a).

9. A method according to claim 1, further comprising prior to step (b) adding a water-miscible organic solvent to the nitrosamine-containing reaction mixture obtained in step (a).

10. A method according to claim 9, wherein said water-miscible organic solvent is a lower alcohol.

11. A method according to claim 1, wherein the reaction mixture in step (b) is cooled to maintain its temperature within the range from about 0° to about 30° C.

12. A method according to claim 1, wherein in step (b) said metallic zinc is added in portions into a nitrosamine derivative containing reaction solution already containing a sufficient quantity of acid, and the zinc is added sufficiently slowly to enable the temperature of the reaction mixture to be maintained within the range from about 0° to about 30° C.

13. A method according to claim 1, wherein after addition metallic zinc in step (b), acid is added in portions to assure the presence of a sufficient quantity of acid in the reaction mixture, and the acid is added sufficiently slowly to enable the temperature of the reaction mixture to be maintained within the range from about 0° to about 30 ° C.

14. A method according to claim 1, wherein in step b) both metallic zinc and acid are added in portions to the nitrosamine derivative containing reaction medium obtained from step a) sufficiently slowly to maintain the temperature of the reaction mixture within the range from about 0° to about 30° C.

15. A method according to claim 1, further comprising after the reduction of the nitrosamine to the corresponding hydrazine in step b), the step of adding sufficient additional acid to assure complete reaction of any excess of metallic zinc present in the reaction mixture.

16. A method according to claim 1, wherein the acids used are individually selected from the group consisting of acetic acid and aqueous hydrochloric acid solution.

17. A method according to claim 1, wherein compounds of Formula II are used wherein R[2] and R[3] together form an alkylene chain containing 2 to 4 carbon atoms and optionally substituted by lower alkyl.

* * * * *